United States Patent [19]

Gresl et al.

[11] Patent Number: 5,104,381
[45] Date of Patent: Apr. 14, 1992

[54] PNEUMONEEDLE WITH REMOVABLE STYLET ASSEMBLY

[75] Inventors: Charles Gresl, San Francisco; Terrance L. Kloeckl, Palo Alto, both of Calif.

[73] Assignee: Origin Medsystems, Inc., San Mateo, Calif.

[21] Appl. No.: 753,409

[22] Filed: Aug. 30, 1991

[51] Int. Cl.⁵ .............................. A61M 5/178
[52] U.S. Cl. ............................ 604/164; 604/26; 604/51
[58] Field of Search ........... 604/164, 165, 167, 51, 604/26, 170, 274; 128/754

[56] References Cited

U.S. PATENT DOCUMENTS

| | | |
|---|---|---|
| 1,527,291 | 2/1925 | Zorraquin . |
| 2,623,521 | 12/1952 | Shaw .................................... 128/221 |
| 3,713,447 | 1/1973 | Adair .................................... 128/347 |
| 3,774,604 | 11/1973 | Danielsson ........................ 128/214.4 |
| 4,314,565 | 2/1982 | Lee ...................................... 128/754 |
| 4,403,617 | 9/1983 | Tretinyak ............................ 128/754 |
| 4,535,773 | 8/1985 | Yoon ...................................... 604/51 |
| 4,655,226 | 4/1987 | Lee ...................................... 128/754 |
| 4,735,215 | 4/1988 | Goto et al. ............................ 128/754 |
| 4,808,168 | 2/1989 | Warring ................................ 604/158 |
| 4,869,717 | 9/1989 | Adair .................................... 604/164 |
| 4,907,599 | 3/1990 | Taylor .................................. 128/754 |
| 5,036,860 | 8/1991 | Leigh et al. .......................... 128/754 |

Primary Examiner—Gene Mancene
Assistant Examiner—Michael Lynch
Attorney, Agent, or Firm—Limbach & Limbach

[57] ABSTRACT

An improved pneumoneedle wherein the stylet forms part of an assembly removably received within the needle housing. The assembly carries a valve to selectively open or close the needle to fluid flow. The stylet is slidably carried by the assembly and resiliently biased to extend through the needle. Removal of the assembly opens the needle. A septum is engagable with the housing to seal the needle when the assembly is removed. A viewable indicator carried by the stylet signals when the needle has completed penetration.

22 Claims, 3 Drawing Sheets

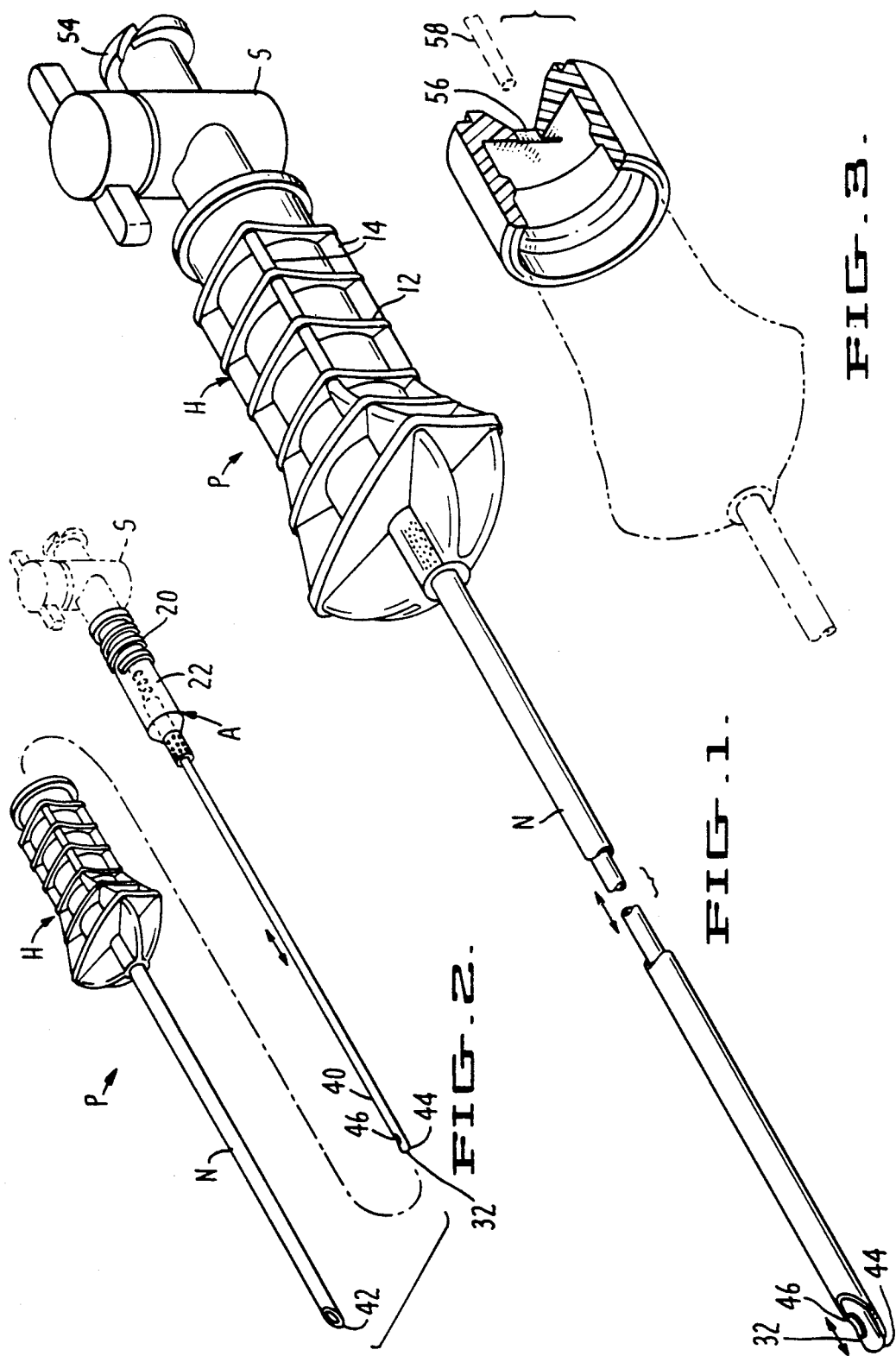

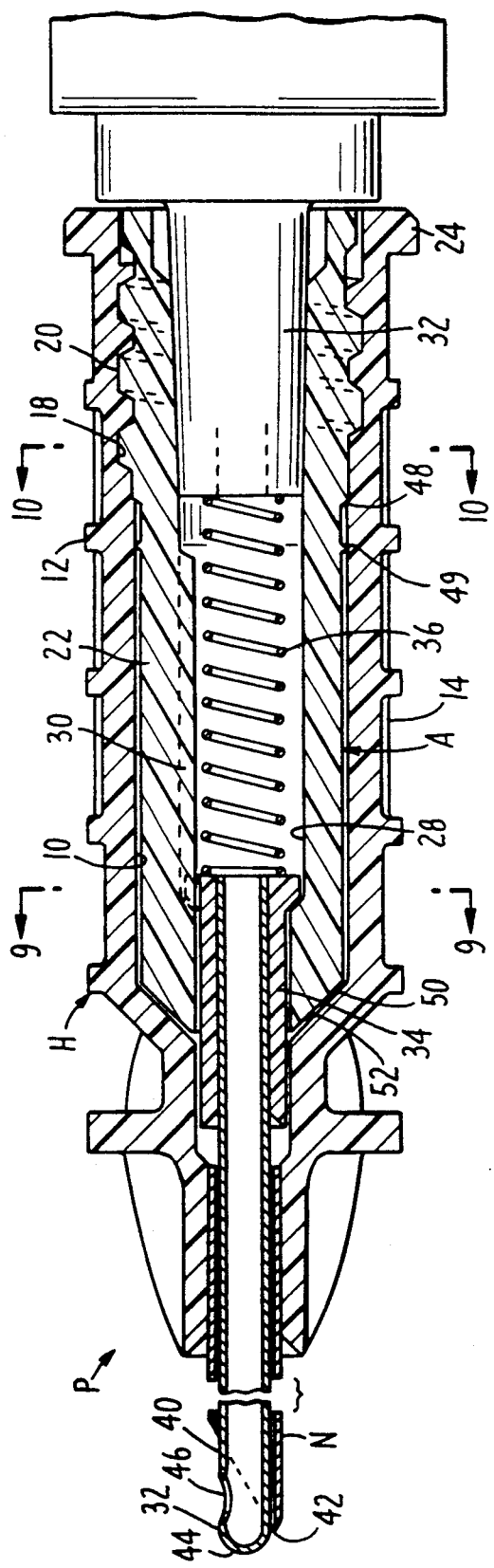
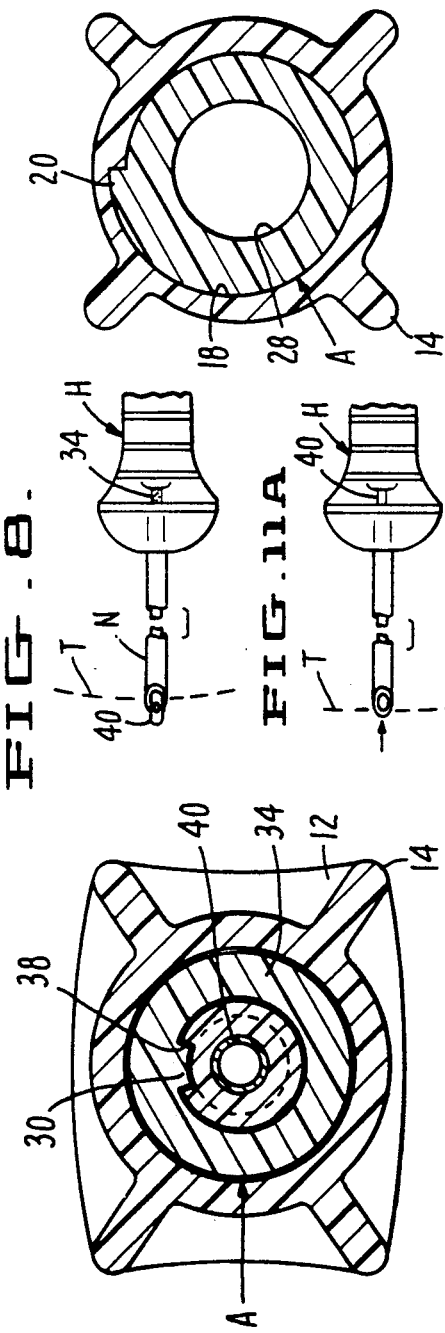

PNEUMONEEDLE WITH REMOVABLE STYLET ASSEMBLY

BACKGROUND OF THE INVENTION

The present invention relates to a Veress-type pneumoneedle and, more particularly, is directed to such a needle which may be of the single use disposable type. In its more specific aspects, the invention is concerned with a pneumoneedle in which the stylet of the needle forms part of an assembly which may be removed to open the needle.

Veress-type pneumoneedles have a spring-loaded stylet which is slidably received within a hollow needle. In use for abdominal endoscopy, once the pneumoneedle penetrates the abdominal wall and enters the cavity, resistance against the end of the needle ceases and a spring pushes the blunt end of the stylet beyond the sharp tip of the needle.

The pneumoneedles introduced by Veress in the late 1930s were reusable. The stylets in such needles carry a valve assembly which is pushed rearward by the resistance on the needle end and is biased forwardly by a spring when the resistance is removed. With this design, the body of the needle must be grasped forwardly of the valve assembly to avoid imparting force to the stylet.

U.S. Pat. No. 4,808,168 discloses a disposable pneumoneedle wherein the valve assembly is fixed to a housing which slidably carries the stylet. A spring within the housing biases the stylet forwardly through the needle and permits the stylet to retract upon encountering resistance. Because the valve assembly is carried by the housing, rather than the stylet, force applied to the assembly does not interfere with such retraction of the stylet.

In the pneumoneedle of U.S. Pat. No. 4,808,168, the needle, housing, stylet, spring and valve form an assembly which cannot be taken apart, without destruction. As a result, the stylet is always disposed within the needle and cannot be removed to permit access through the needle.

SUMMARY OF THE INVENTION

In the pneumoneedle of the present invention, the needle is secured to a handle having a longitudinal bore. The stylet forms part of an assembly removably received within the bore. Interengagable means on the stylet assembly and handle are provided to releasably secure the assembly within the bore and maintain the stylet in a condition extending through the needle. Valve means is carried by the assembly for selectively opening and closing the assembly to fluid flow and seal means is provided to establish sealed communication between the stylet assembly and needle when the assembly is received within the bore.

The stylet assembly is fully removable from the handle to open the needle. A septum is engagable with the handle to seal the bore when the assembly is removed.

A principal object of the invention is to provide a Veress-type pneumoneedle wherein the stylet may be removed from the needle to permit access therethrough.

Another and more specific object of the invention is to provide such a pneumoneedle wherein the stylet is carried by an assembly which is removable from the handle for the needle.

Still another object of the invention is to provide such a pneumoneedle wherein valve means is carried by the stylet assembly in such a way that external force applied to the valve means during use of the needle does not interfere with retraction of the stylet into the needle.

A further object of the invention is to provide such a pneumoneedle wherein, when the stylet assembly is received within the handle, the stylet is guided for aligned rectilinear movement relative to the needle.

A further object of the invention is to provide such a pneumoneedle with a septum which serves to seal the passage through the needle when the stylet assembly is removed.

Another and more specific object of the invention is to provide such a pneumoneedle wherein the stylet assembly assumes a condition sealed to the housing when received therein.

Another object of the invention is to provide a pneumoneedle with viewable means which serves to indicate when the needle has completed penetration.

Yet another and more general object of the invention is to provide such a pneumoneedle which is of a disposable and relatively inexpensive construction.

These and other objects will become more apparent when viewed in light of the following detailed description and accompanying drawings.

BRIEF DESCRIPTION OF THE DRAWINGS

FIG. 1 is a perspective view of the inventive pneumoneedle in the fully assembled condition, with parts thereof broken away;

FIG. 2 is an exploded perspective view of the inventive pneumoneedle, with the stylet assembly in the removed condition;

FIG. 3 is a perspective view of the septum used to seal the needle housing when the stylet assembly is removed, with phantom lines illustrating the housing and needle and an elongate element positioned for passage through the septum and into the needle;

FIG. 8 is a cross-sectional longitudinal view of the pneumoneedle, with the stylet assembly received within the needle housing;

FIGS. 9 and 10 are cross-sectional views taken on the planes designated by lines 9—9 and 10—10, respectively, of FIG. 8; and, FIGS. 11A and 11B are plan views of the inventive pneumoneedle, illustrating the viewable indicator carried by the stylet hub to indicate when the needle has completed penetration.

DESCRIPTION OF THE PREFERRED EMBODIMENT

The assembled pneumoneedle is shown in FIGS. 1 and 8 and designated in its entirety by the letter "P". It comprises, as its basic elements: a needle "N"; a transparent handle "H" having a longitudinal bore 10 formed therein; a stylet assembly "A" receivable within the bore 10; and, a stopcock "S" secured to the assembly "A".

Figure 5:
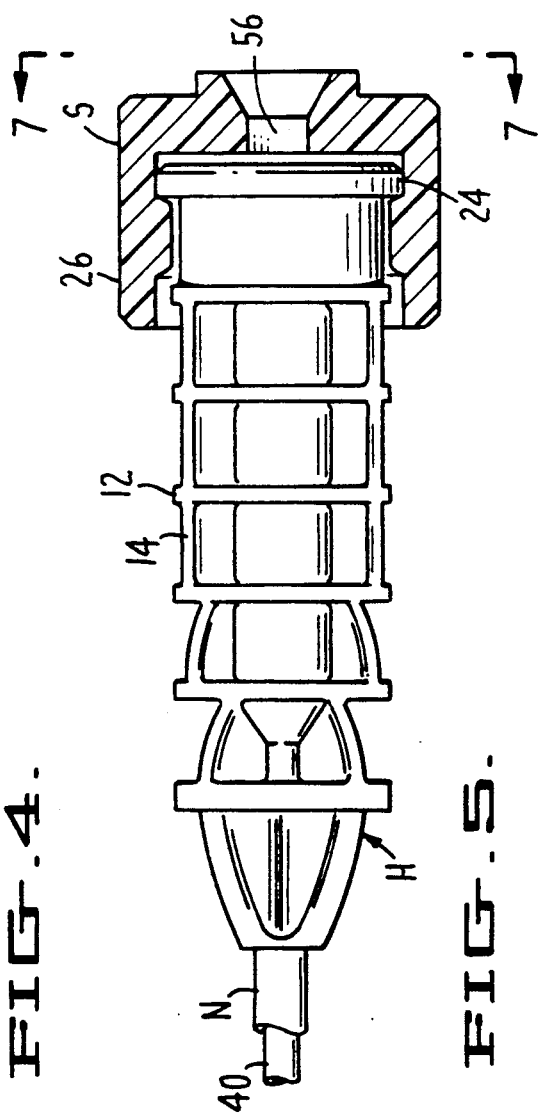
FIG. 5 is a longitudinal view of the needle housing, with the stylet assembly removed therefrom and a septum secured to the housing.

The handle "H" is formed with transverse ribs 12 and longitudinal ribs 14 on the external surface thereof. The needle "N" is fixedly secured within a passage 16 extending through the handle into communication with the bore 10. The interior of the bore 10 is formed with screw threads 18 for complemental receipt of mating screw threads 20 formed on the housing 22 of the stylet assembly "A". The bore 10 Opens through the proximal end of the handle "H". A collar 24 is formed around the proximal end of the handle for engagement by a septum 26, as may be seen from FIG. 5.

The housing 22 is formed with a throughbore 28 having a key 30 extending over the length of its intermediate portion (see FIGS. 8 and 9). The proximal portion of the throughbore 28 is outwardly tapered and receives the nozzle 32 of the stopcock "S". In the assembled condition, the nozzle 32 is fixedly adhered within the throughbore A stylet hub 34 is slidably received within the throughbore and normally biased outwardly by a compression coil spring 36 interposed between the nozzle 32 and the hub. The hub is formed with a keyway 38 for slidable receipt of the key 30 (see FIG. 9). A stylet 40 is fixed within the hub 34 and proportioned to extend through the full length of the needle "N" and slightly beyond the sharpened distal tip of the needle, designated 42. The distal end of the stylet, designated 44 is of a closed rounded configuration. A laterally extending opening 46 is formed in the stylet adjacent the end 44.

From FIG. 8 it will be seen that the distal tip of the needle "N" is cut at a bias (see the dotted lines) so as to have a laterally open side. The opening 46 aligns with this open side. Key 30 and mating keyway 38 maintain this alignment.

When fully threaded into place within the handle "H" as shown in FIG. 8, the stylet assembly seats against the handle at 48. A seal is provided between the handle and housing by a thin collar 49 formed on the housing 22 for sealed engagement with the internal surface of the throughbore 28. From FIG. 8 it will also be seen that the distal end of the housing 22 is formed with a tapered surface 50 complemental with a tapered surface 52 in the throughbore 28. These surfaces may provide for sealing between the housing 22 and handle "H" in addition, or as an alternative, to the seal provided by the collar 49.

The housing 22 is opaque over at least the distal portion thereof which slidably receives the stylet hub 34. The hub 34 is of a contrasting opaque color. In a typical embodiment, the housing 22 is black and the hub 34 red. When the stylet 40 extends from the distal end of the needle "N", the red hub 34 may be visually observed, as seen in FIG. 11A. Depression of the stylet serves to move the hub into a hidden condition within the housing 22, as seen in FIG. 11B. The transparent character of the handle "H" enables the position of the hub 34 to be visually observed.

OPERATION

In use, the stylet assembly is first screwed into the handle "H" to the fully seated condition shown in FIG. 8. The pneumoneedle is then pushed through the body tissue to be penetrated ("T" in FIGS. 11A and 11B). During the course of penetration, the stylet 40 retracts in response to the resistance of the tissue and the hub 34 retracts to the hidden condition shown in FIG. 11A. Upon penetrating the cavity to be accessed, the rounded distal end 44 of the stylet snaps beyond the distal tip 42 of the needle to shield the tip and the hub 34 assumes the visually observable position shown in FIG. 11B. Insufflating gas may then be introduced into the cavity through the stopcock "S". A conventional fitting 54 on the stopcock "S" is provided for connection to a gas conduit.

Figure 7:
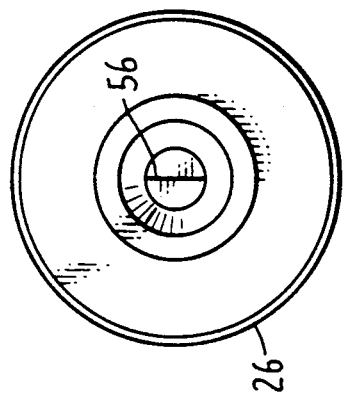
FIG. 7 is plan view of the septum, taken on the plane designated by line 7—7 of FIG. 5.
Figure 6:
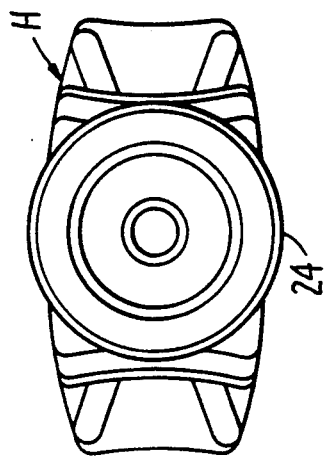
FIG. 6 is an end view of the needle housing, with the stylet assembly removed.
Figure 4:
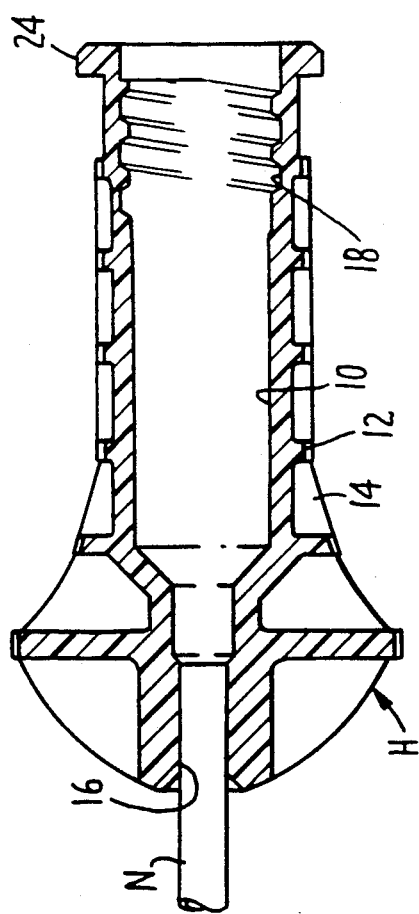
FIG. 4 is a cross-sectional longitudinal view of the needle housing, with the stylet assembly removed therefrom.

If it is desired to access the interior of the cavity through the pneumoneedle, the stylet assembly "A" is screwed out of the handle "H", thus leaving the needle open, as seen in FIG. 4. The septum 26 is then engaged over the collar 24 to seal the handle. A slit 56 formed in the septum provides a passage through which an elongate object, such as a catheter or fiberoptic element, may be extended. Such an element is depicted by the numeral 58 in FIG. 3. The septum 26 may be removed and the stylet assembly reinstalled for further insufflation.

The ribs 12 and 14 facilitate gripping and orientation of the handle "H". It should also be appreciated that axial forces applied to the stopcock "S" in no way restrict the freedom of the stylet 40 to move back and forth within the needle.

CONCLUSION

In the preferred embodiment, the metallic parts of the pneumoneedle (needle "N", stylet 40, and spring 36) are fabricated of stainless steel. The septum 26 is made of an elastomeric rubber material, such as silicone. The remaining parts of the pneumoneedle are made of relatively inexpensive plastic material, such as polycarbonate.

The pneumoneedle is unique in that it is both ideally designed for use as a disposable item, and also provides for removal of the stylet and access through the needle. It also has the advantage that axial forces applied to the stopcock do not interfere with reciprocation of the stylet within the needle and that the hub 34 serves as a visually observable indicator to indicate when the needle has completed penetration.

It should be appreciated that the invention is not intended to be limited to the specifics of the illustrated embodiment, but rather is defined by the accompanying claims.

We claim:

1. A pneumoneedle comprising:
   a) a handle having a longitudinal bore;
   b) a hollow needle secured to the handle and opening into the bore, said needle being adapted for penetrating a body cavity and providing a conduit into the cavity;
   c) a housing engagable with the handle in alignment with the bore;
   d) a stylet slidably received within the housing and for extension through the needle upon engagement of the housing with the handle;
   e) biasing means within the housing to resiliently urge the stylet outwardly relative to the housing;
   f) interengagable means on the housing and handle to releasably secure the housing in engagement with the handle and maintain the stylet in a condition extending through the needle;
   g) valve means carried by the housing for selectively opening and closing the housing to fluid flow therethrough; and,
   h) seal means to establish a sealed connection between the needle and valve means when the handle and housing are engaged.

2. A pneumoneedle according to claim 1 wherein the housing is engagable within the bore of the handle and the interengagable means comprises complemental screw threads formed o the housing and bore.

3. A pneumoneedle according to claim 1 wherein, when extended through the needle, the stylet permits the fluid flow through the needle.

4. A pneumoneedle according to claim 1 wherein:
a) the needle has a sharp distal tip;
b) the stylet is proportioned for extension fully through the needle and has a distal end extensible beyond the distal tip of the needle when the housing is engaged with the handle and the biasing means extends the stylet outwardly relative to the housing; and,
c) the biasing means permits the distal end of the stylet to retract within the distal tip of the needle in response to the application of force to the end.

5. A pneumoneedle according to claim 4 further comprising indicator means operatively associated with the stylet to signal when the stylet extends beyond the distal tip of the needle.

6. A pneumoneedle according to claim 5, wherein the indicator means comprises:
a) an indicator element carried by the stylet for longitudinal movement therewith, said element being visually observable when the distal end of the stylet extends beyond the distal tip of the needle; and,
b) a shield on the housing to shield the indicator element from visual observation when the stylet is retracted within the distal tip of the needle in response to the application of force to the distal end of the stylet.

7. A pneumoneedle according to claim 6 wherein the handle is transparent to enable the indicator element to be viewed therethrough when the stylet extends beyond the distal tip of the needle.

8. A pneumoneedle according to claim 4 wherein the distal tip of the needle is laterally open on one side and the stylet is tubular and has a lateral opening closely adjacent the distal end; said pneumoneedle further comprising means to maintain the opening in the stylet in alignment with the laterally open side of the needle.

9. A pneumoneedle according to claim 1 wherein the housing and stylet are removable from the handle as a unit to leave the bore and needle in an unobstructed condition.

10. A pneumoneedle according to claim 9 further comprising a septum engagable with the handle to seal bore when the housing and stylet are removed from the bore.

11. A pneumoneedle according to claim 10 wherein the septum is fabricated of an elastomeric material and has a slit formed therein to permit the passage of elongate objects therethrough and into the needle.

12. A pneumoneedle comprising:
a) a handle having a longitudinal bore;
b) a hollow needle secured to the handle and opening into the bore, said needle being adapted for penetrating a body cavity and providing a conduit into the cavity;
c) a stylet assembly removably receivable within bore, said assembly comprising a housing and a stylet carried by the housing for longitudinal movement relative thereto and extension through the needle;
d) biasing means within the housing to resiliently urge the stylet outwardly relative to the housing;
e) interengagable means on the handle and the stylet assembly to releasably secure the assembly within the bore and maintain the stylet in a condition extending through the needle;
f) valve means carried by the assembly for selectively opening and closing the assembly to fluid flow therethrough; and
g) seal means to establish sealed communication between the stylet assembly and needle when the assembly is received within the bore.

13. A pneumoneedle according to claim 12 wherein the interengagable means comprises complemental screw threads formed on the housing and bore.

14. A pneumoneedle according to claim 12 wherein:
a) passage means within the housing permits the flow of fluid through the housing; and,
b) the valve means is disposed to selectively open and close the passage means to the flow of fluid.

15. A pneumoneedle according to claim 12 wherein:
a) the needle has a sharp distal tip;
b) the stylet is proportioned for extension fully through the needle and has a distal end extensible beyond the distal tip of the needle when the assembly is received within the bore and the biasing means extends the stylet outwardly relative to the housing; and,
c) the biasing means permits the distal end of the stylet to retract within the distal tip of the needle in response to the application of force to the end.

16. A pneumoneedle according to claim 15 wherein the distal tip of the needle is laterally open on one side and the stylet is tubular and has a lateral opening closely adjacent the distal end; said pneumoneedle further comprising means to maintain the opening in the stylet in alignment with the laterally open side of the needle.

17. A pneumoneedle according to claim 15 further comprising indicator mean operatively associated with the stylet to signal when the stylet extends beyond the distal tip of the needle.

18. A pneumoneedle according to claim 17, wherein the indicator means comprises:
a) an indicator element carried by the stylet for longitudinal movement therewith, said element being visually observable when the distal end of the stylet extends beyond the distal tip of the needle; and,
b) a shield on the housing to shield the indicator element from visual observation when the stylet is retracted within the distal tip of the needle in response to the application of force to the distal end of the stylet.

19. A pneumoneedle according to claim 18 wherein the handle is transparent to enable the indicator element to be viewed therethrough when the stylet extends beyond the distal tip of the needle.

20. A pneumoneedle according to claim 12 wherein the assembly is removable from the bore as a unit to leave the bore and needle in an unobstructed condition.

21. A pneumoneedle according to claim 20 further comprising a septum engagable with the handle to seal bore when the assembly is removed from the bore.

22. A pneumoneedle according to claim 21 wherein the septum is fabricated of an elastomeric material and has a slit formed therein to permit the passage of elongate objects therethrough and into the needle.

* * * * *

UNITED STATES PATENT AND TRADEMARK OFFICE
CERTIFICATE OF CORRECTION

PATENT NO. : 5,104,381
DATED : April 14, 1992
INVENTOR(S) : CHARLES (NMI) GRESL and TERRANCE L. KLOECKL It is certified that error appears in the above - identified patent and that said Letters Patent is hereby corrected as shown below:

In Col. 5, Line 2, "o" should be "on"

In Col. 6, Line 39, "mean" should be "means"

Signed and Sealed this

Sixth Day of July, 1993

Attest:

MICHAEL K. KIRK

Attesting Officer

Acting Commissioner of Patents and Trademarks